United States Patent [19]

Sinn

[11] Patent Number: 5,249,673
[45] Date of Patent: Oct. 5, 1993

[54] PACKAGE AND METHOD OF LOADING FOR RESILIENT SURGICAL SUTURES

[75] Inventor: Hans-Jurgen F. Sinn, Fairfield, Conn.

[73] Assignee: United States Surgical corporation, Norwalk, Conn.

[21] Appl. No.: 856,248

[22] Filed: Mar. 25, 1992

Related U.S. Application Data

[63] Continuation-in-part of Ser. No. 832,376, Feb. 7, 1992.

[51] Int. Cl.⁵ .............................................. A61L 17/02
[52] U.S. Cl. .................................. 206/63.3; 206/382; 206/388
[58] Field of Search .................... 206/63.3, 63.5, 227, 206/380, 388, 389, 403, 408, 409, 467, 471, 574, 382; 53/449, 453

[56] References Cited

U.S. PATENT DOCUMENTS

| | | |
|---|---|---|
| 2,615,565 | 10/1952 | Bower et al. |
| 3,972,418 | 8/1976 | Schuler et al. ..................... 206/63.3 |
| 4,424,898 | 1/1984 | Thyen et al. ........................ 206/380 |
| 4,961,498 | 10/1990 | Kalinski et al. ..................... 206/480 |
| 4,967,902 | 11/1990 | Sobel et al. ......................... 206/380 |
| 5,056,658 | 10/1991 | Sobel et al. ........................ 206/63.3 |
| 5,099,994 | 3/1992 | Kalinski et al. .................... 206/63.3 |

FOREIGN PATENT DOCUMENTS

2161130 1/1986 United Kingdom .............. 206/63.3

Primary Examiner—Jimmy G. Foster
Attorney, Agent, or Firm—Thomas R. Bremer; Peter G. Dilworth; Rocco S. Barrese

[57] ABSTRACT

A package is provided for retaining at least one armed surgical suture including housing means having suture retention means formed therein and a needle securement area integrally formed in the housing means At least one porthole is defined in the needle securement area which is dimensioned and positioned for maintaining a surgical needle for ready removal.

14 Claims, 6 Drawing Sheets

PACKAGE AND METHOD OF LOADING FOR RESILIENT SURGICAL SUTURES

CROSS-REFERENCE TO RELATED APPLICATION

This application is a continuation-in part of applicant's copending application Ser. No. 07/832,376 filed on Feb. 7, 1992.

BACKGROUND OF THE INVENTION

1. Field of the Invention

The invention relates to a new and useful package for retaining surgical sutures and more particularly to retainer packages with integral needle holders adapted for retaining armed sutures therein.

2. Description of the Related Art

Many packages for retaining surgical sutures comprise structural portions which are adapted to be assembled subsequent to being loaded with sutures.

Prior art packages manufactured in such a manner include those shown in U.S. Pat. Nos. 4,424,898, 4,961,498, and 4,967,902. Each of these packages has a retainer portion into which surgical sutures can be loaded and another structural portion which may be fastened to the retainer portion subsequent to loading the sutures so as to complete construction of the package. In addition, each of these packages is manufactured with upstanding projections formed in the retainer portion around which sutures may be wound. These winding projections are generally unsuited for receiving resilient monofilament sutures which can take an undesirable set when forced to conform around winding posts.

With the present invention, manufacturing efficiencies may be realized when resilient surgical sutures are loaded into pre-constructed retainer packages which are formed without winding projections. In accordance with this principle, it is an object of the subject invention to provide an inexpensive retainer package which can be easily and quickly loaded with at least one resilient surgical suture subsequent to having been constructed.

It is a further object of the subject invention to provide a package for retaining a plurality of resilient surgical sutures for ready removal.

It is another object of the subject invention to provide a package for retaining a plurality of armed surgical sutures.

It is yet another object of the subject invention to provide a package having an integrally formed needle park with at least one porthole for receiving a surgical needle.

SUMMARY OF THE INVENTION

A package is provided for retaining at least one resilient surgical suture. The package comprises a base member which has an annular recessed portion formed therein. A circumjacent flexible flange portion extends outward from the recessed portion of the base member. The package further comprises an annular cover member which is mounted adjacent to the recessed portion of the base member to form a peripheral retaining channel in the annular recessed of the base member. The annular recessed portion of the base member is preferably elliptical in configuration and the cover member is of a similar elliptical configuration. Furthermore, the cover member is preferably formed with a tunnel which extends at least partially about the periphery thereof.

The package may be constructed by providing a plurality of upstanding bosses in the recessed portion of the base member spaced from the periphery thereof and by further providing a plurality of corresponding apertures on the cover member in which the bosses may be engaged so as to mount the cover member adjacent to the recessed portion. Alternatively, the cover member may be mounted adjacent the recessed portion of the base member by applying sonic weldments or glue to each member at corresponding locations spaced from each members periphery.

Where armed sutures are to be packaged, the retainer of the subject invention may further comprise needle park means which would include a needle park housing formed in the elliptical cover member of the package and which may be disposed proximate to the minor diametric axis thereof. The needle park means may further include a sponge member disposed in the housing and preferably accessible through a port. The sponge member is maintained in the needle park housing by mounting the cover member to the base member upon constructing the package.

In a preferred embodiment of the subject invention, the needle park means may comprise an integral needle securement area which is monolithically formed with the annular cover member of the retainer package. The needle securement area would have an upstanding wall section including at least one circular porthole for receiving a surgical needle. In one instance, a sponge member may be disposed within the needle securement area for securely maintaining a surgical needle extended through a porthole. Alternatively, a porthole itself may be dimensioned in such a manner so as to securely maintain a surgical needle for ready removal.

The retainer package of the subject invention may be loaded by bending the circumjacent flexible flange portion of the package away from the cover member so as to expose the peripheral retaining channel. Thereafter, a surgical suture may be directed into the peripheral retaining channel. The loading method further includes the step of causing the circumjacent flexible flange portion of the base member to return to its unbent condition so as to seal the retaining channel thereby enclosing the surgical suture within the retainer package.

Further features of the subject invention will become more apparent from the accompanying drawings and the following detailed description of the invention.

BRIEF DESCRIPTION OF THE DRAWINGS

Preferred embodiments of the invention will be described herein below with reference to the drawings wherein.

PREFERRED EMBODIMENT OF THE SUBJECT INVENTION

Figure 1:
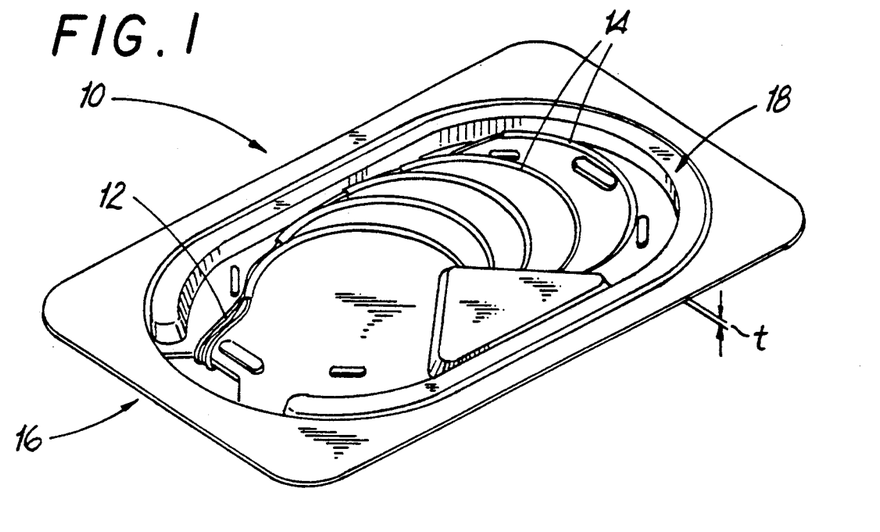
FIG. 1 is a perspective view of a preferred embodiment of a suture retainer package in accordance with the subject invention.
Figure 2:
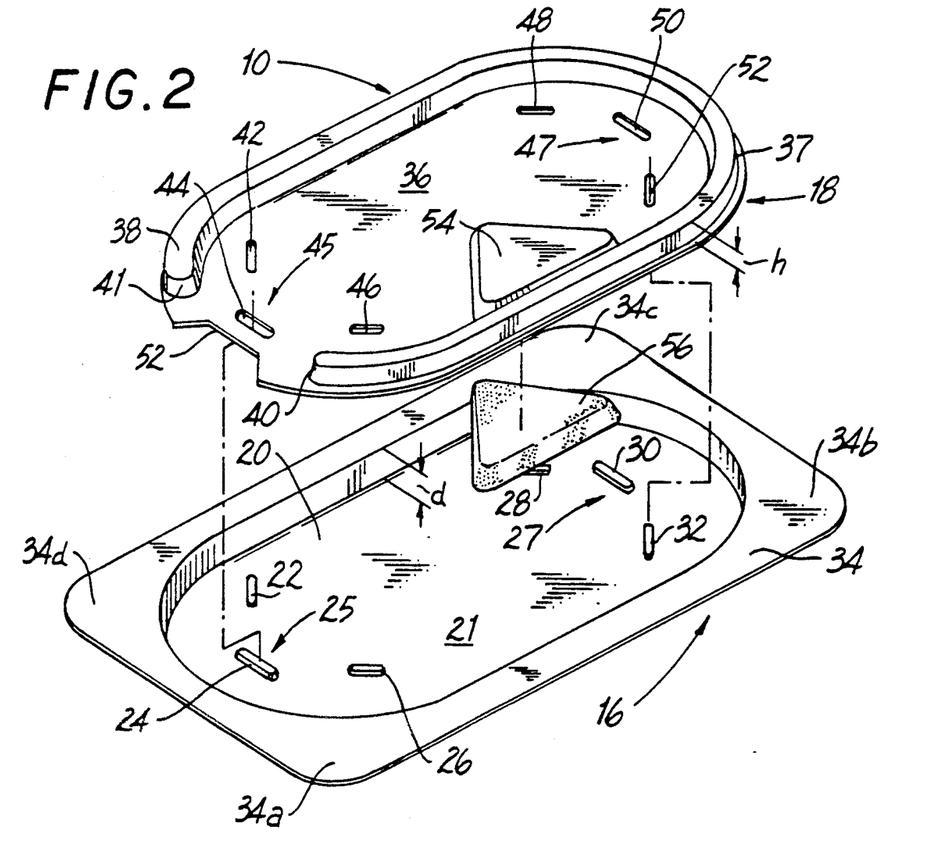
FIG. 2 is an exploded view of the suture retainer package shown in FIG. 1.

A preferred embodiment of the retainer package of the subject invention is illustrated in FIGS. 1 and 2 and is designated generally by reference numeral 10. Retainer package 10 is particularly adapted for receiving and retaining a plurality of resilient surgical sutures 12 each having a surgical needle 14 affixed at one end.

The retainer package 10 comprises a base member 16 and an annular cover member 18, both of which are preferably vacuum formed from polyethylene to a preferred thickness of about 0.013" such that the thickness "t" of the entire package 10 is about 0.2". Other similar materials of construction may be envisioned to manufacture the retainer package 10 of the subject invention.

Referring to FIG. 2, the base member 16 includes an annular recessed portion 20 having a bottom surface face 21 and a depth "d" of about 0.19". Recessed portion 20 is substantially elliptical in configuration. A plurality of upstanding bosses are disposed in recessed portion 20. The bosses are arranged in two spaced apart sets and include a first set 25 having upstanding bosses 22, 24, and 26 and a second set 27 having upstanding bosses 28, 30, and 32.

A circumjacent flexible flange portion 34 extends outward from the peripheral edge of the annular recessed portion 20. Flange portion 34 includes first through fourth flexible panels 34a–34d.

The annular cover member 18 of retainer package 10 is substantially elliptical in configuration and may be mounted adjacent to the recessed portion 20 of base member 16. Cover member 18 includes a planar surface face 36 having a peripheral edge 37. A tunnel 38 having a generally inverted U-shaped cross section extends partially about the periphery 37 of planar surface 36 from a first end 40 to a second end 41. Tunnel 38 has a height "h" which is about 0.18" and is thus substantially equal to the depth "d" of the annular recessed portion 20 of base member 16.

A plurality of slots extend through the planar surface face 36 of cover member 18 and are arranged in two spaced apart sets which correspond to the two spaced apart sets of bosses 25 and 27 and includes a first set 45 having slots 42, 44, and 46 and a second set of slots 47 having slots 48, 50 and 52.

The cover member 48 of retainer package 10 further includes a needle park housing 54 within which a sponge member 56 is provided into which a plurality of surgical needles 14 may be inserted and parked for ready removal.

Figure 3:
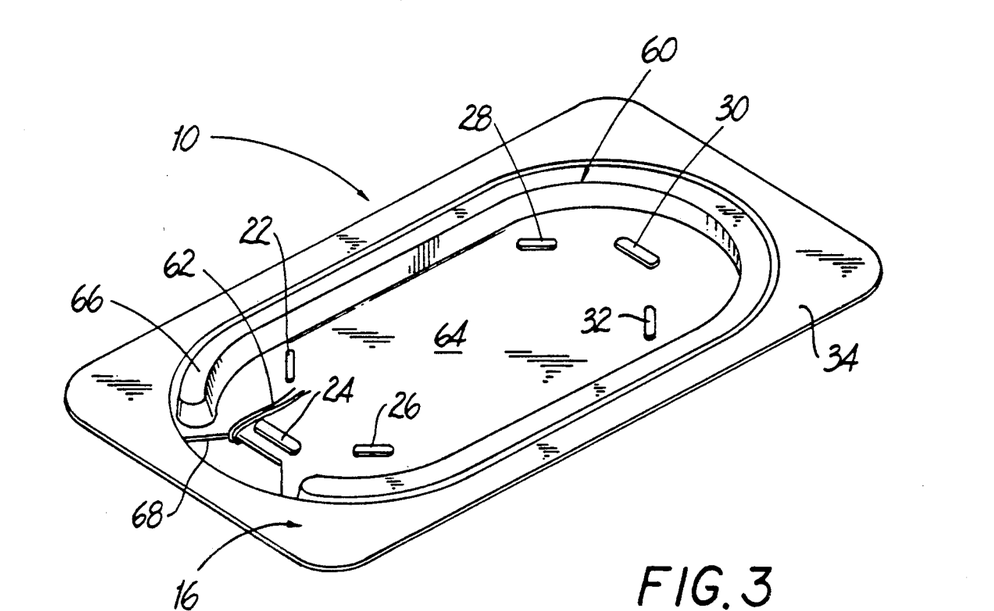
FIG. 3 is an alternate embodiment of the suture retainer package shown in FIG. 1.

Turning to FIG. 3, an alternate embodiment of the retainer package 10 is illustrated which comprises an annular cover member that is designated generally by reference numeral 60. Cover member 60 is to be utilized if the retainer package 10 is employed to accommodate a plurality of unarmed surgical sutures 62. The cover member 60 includes a planar surface face 64 having a tunnel 66 extending partially about the periphery thereof for retaining a plurality of unarmed sutures 62 and further includes a port 68 extending into planar surface face 64 form the periphery thereof for permitting the passage of the unarmed sutures 62 from within the retainer package 10.

Referring again to FIG. 2, the retainer package 10 of the subject invention is constructed by mounting cover member 18 adjacent to the recessed portion 20 of base member 16. Initially, the sponge member 56 may be arranged in the recessed portion 20 of base member 16 so that it can be in registration with the needle park housing 54 formed in cover member 18. Subsequently, the annular cover member 18 is extended into the recessed portion 20 in such a manner so that the first set of upstanding bosses 25 extend through the corresponding set of slots 45 in cover member 18 and similarly the second set of spaced apart bosses 27 extends through the corresponding set of slots 47. Thereupon, planar surface 36 of cover member 18 and bottom surface 21 of base member 16 are disposed in face-to-face contact. At such a time, each of the bosses are snap-fit into a respective slot and are retained therein by friction. Other methods of mounting the cover member 16 adjacent to the base member 18 may be envisioned including sonic welding or glue.

Figure 4:
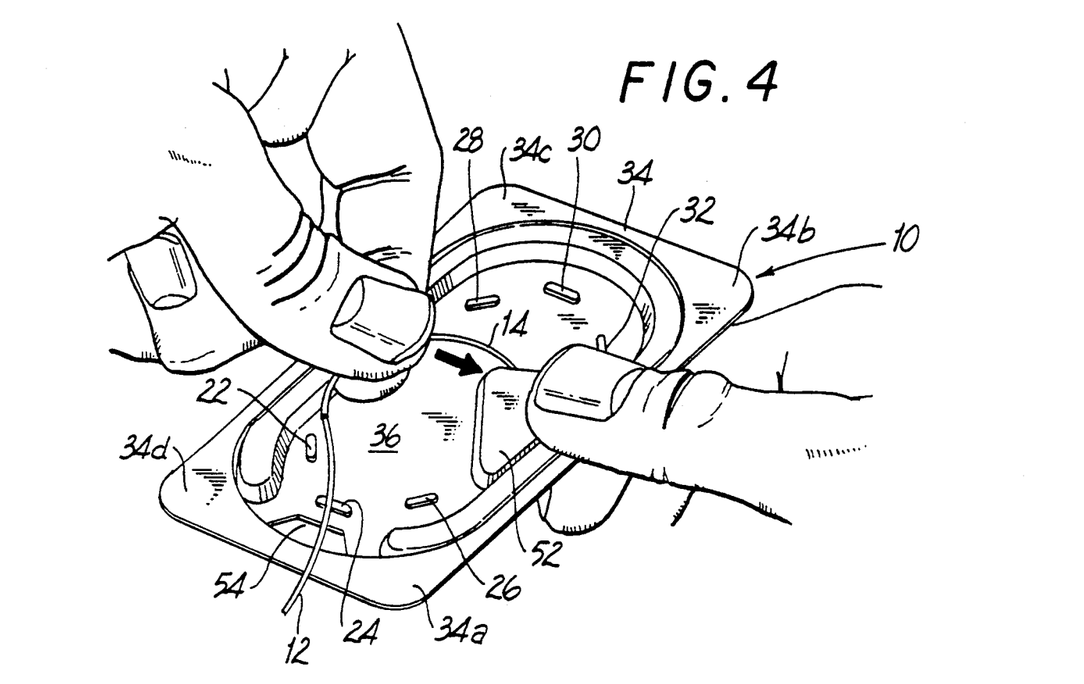
FIG. 4 illustrates the first step in the method of loading the suture retainer package shown in FIG. 1.
Figure 5:
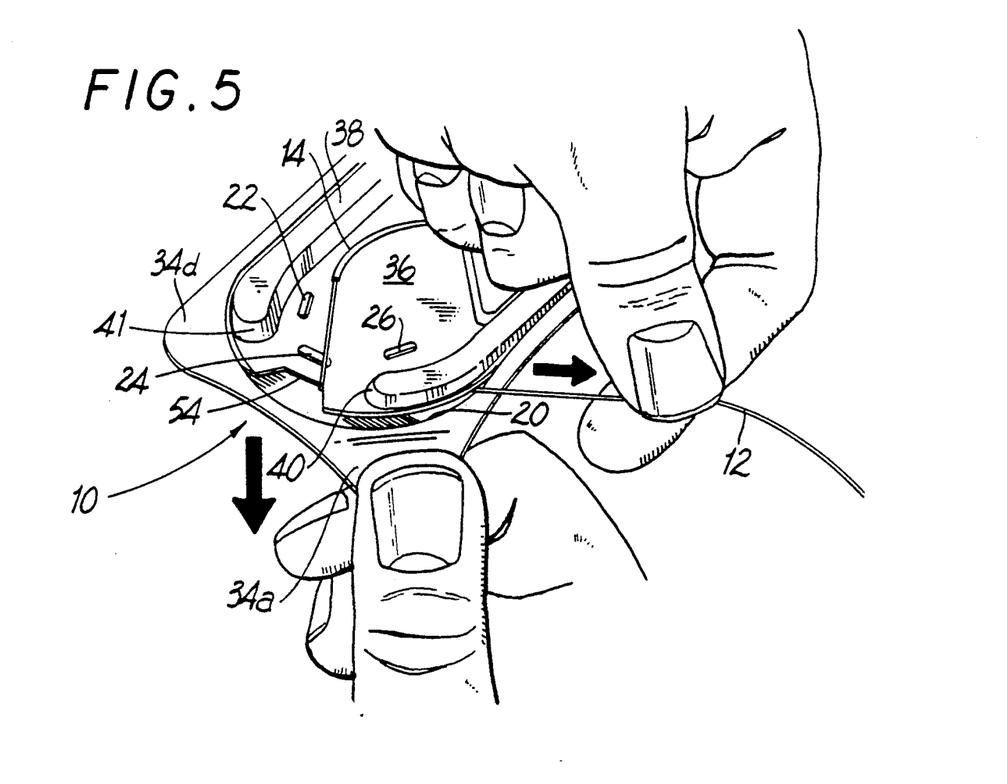
FIG. 5 illustrates a subsequent step in the loading method of the subject invention.
Figure 6:
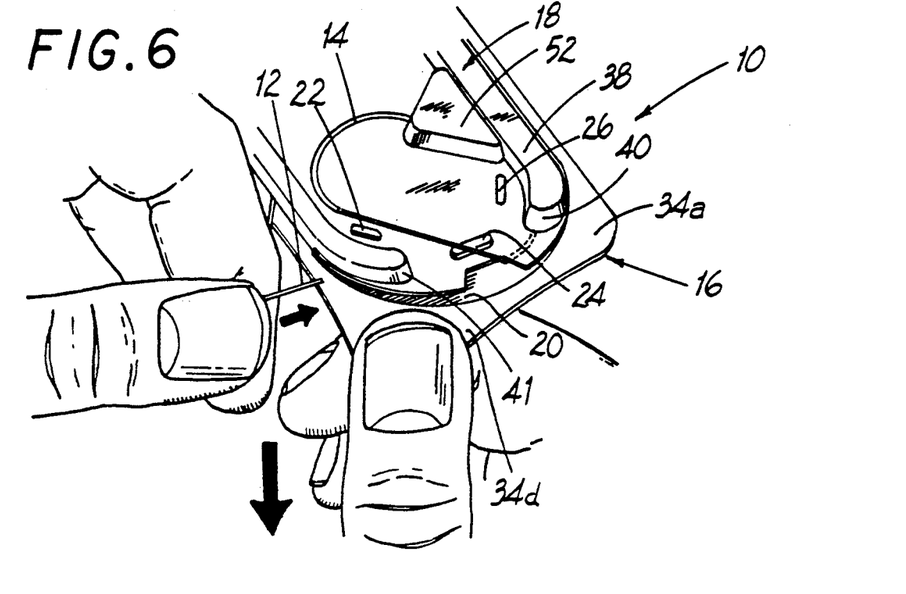
FIG. 6 illustrates a final step in the method of loading the retainer package shown in FIG. 1.

Referring now to FIGS. 4–6, to load the retainer package 10 of subject invention a curved surgical needle 14 is inserted into the sponge member 56 disposed in the needle park housing 54 as illustrated by the indicator arrow in FIG. 4. Thereafter, each of the panels 34a–34d of flange 34 are progressively bent away from the cover member 18 to gradually expose the annular recessed portion 20 of the base member 16. Initially, panel 34a of the flexible flange portion 34 of base member 16 is bent away from the cover member 18 so as to expose a section of the annular recessed portion 20 of base member 16 as illustrated by the indicator arrow in FIG. 5. At this time, suture 12 is directed through the port 54 in cover member 18 and into the exposed section of recessed portion 20. Subsequently, panels 34b and 34c of the flexible flange 34 are progressively bent away from cover member 18 to gradually expose respective sections of the recessed portion 20 of the base member 16 into which suture 12 may be further directed. Finally, panel 34d of flexible flange 34 is bent away from cover member 18 to expose yet another section of the recessed portion 20 into which the end of suture 12 is directed as illustrated by the indicator arrows in FIG. 6. Thereupon, the flexible flange portion 34 is permitted to return to its original position wherein the suture 12 is accommodated in the peripheral tunnel 38 of cover member 18. Moreover, upon releasing the end of resilient suture 12, the suture may be caused to expand radially outward within the peripheral tunnel 38 so as to be maintained therein for ready removal.

Figure 7:
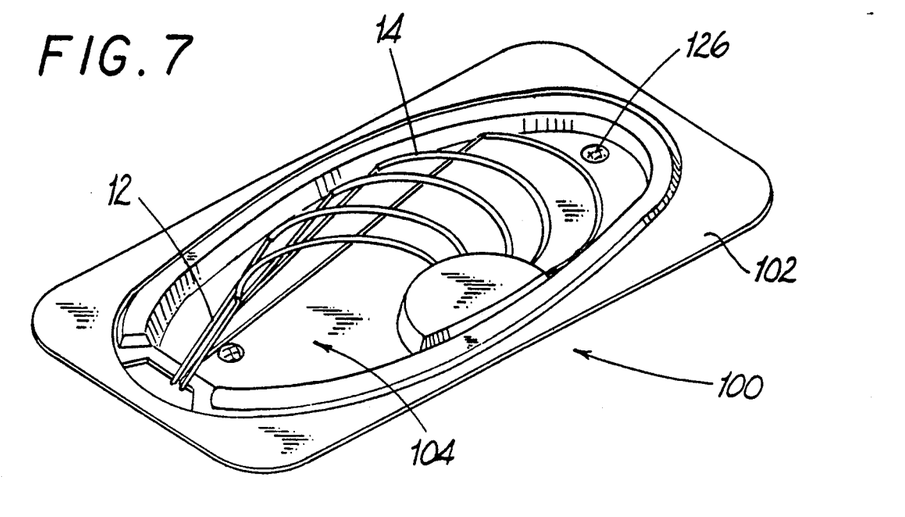
FIG. 7 is a perspective view of a second embodiment of the suture retainer package of the subject invention.
Figure 8:
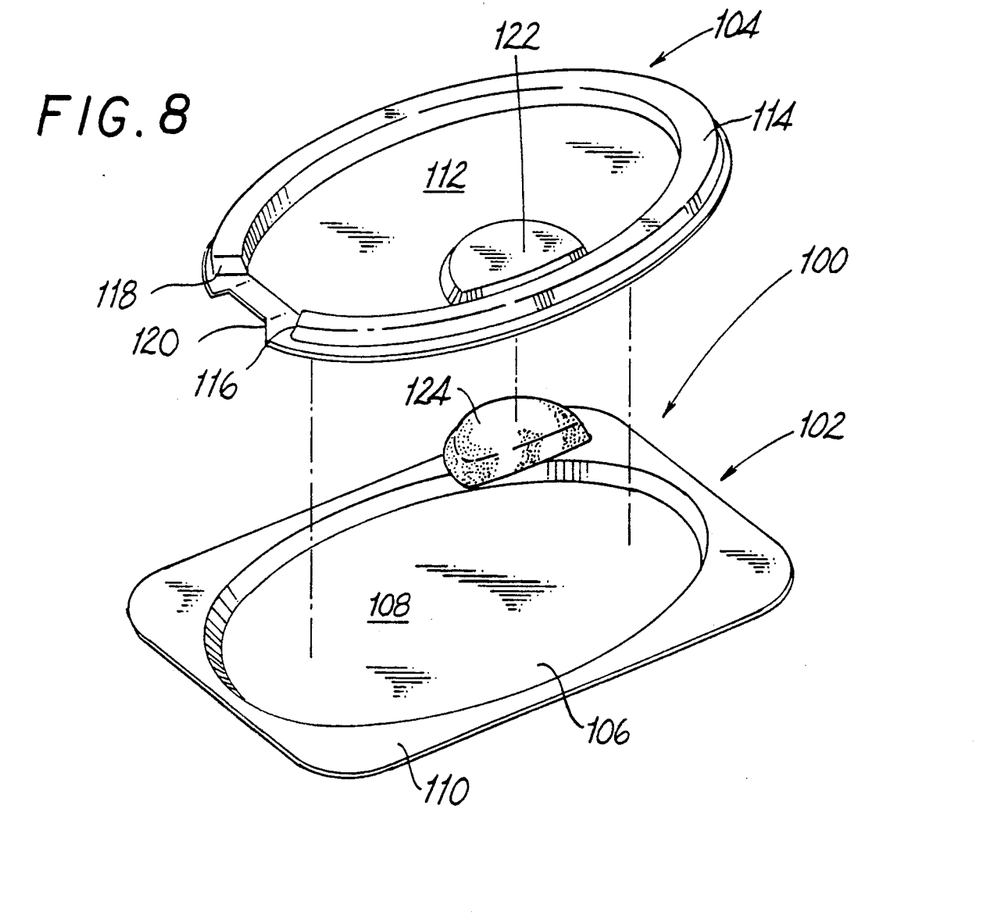
FIG. 8 is an exploded view of the suture retainer package shown in FIG. 7.

Turning now to FIGS. 7 and 8, a second embodiment of the suture retainer package of the subject invention is illustrated and is designated generally be reference numeral 100. Retainer package 100 basically comprises a base member 102 and an annular cover member 104 of substantially elliptical configuration. Base member 102 includes an annular recessed portion 106 of elliptical configuration having a bottom surface face 108. A circumjacent flexible flange portion 110 extends outward from the periphery of the annular recessed portion 106 of base member 102.

Cover member 104 includes a peripheral tunnel 114 which extends partially about the periphery of the planar surface face 112 from a first end 116 to a second end 118. A port 120 extends inward into planar surface face 112 from the periphery thereof intermediate first and second ends 116 and 118 of the tunnel 114 for permitting passage of sutures 12 from within the retainer package 100.

A needle park housing 122 is formed in cover member 112 on the minor diametric axis thereof. A sponge member 124 is disposed in needle park housing 122 and is readily accessible for parking a plurality of suture needles 14 for ready removal.

Figure 10:
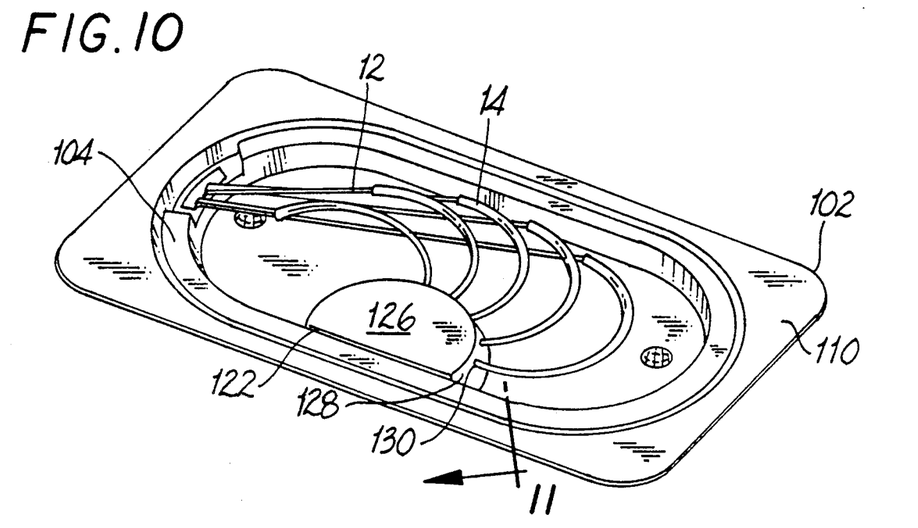
FIG. 10 is a perspective view of the suture retainer package of FIG. 1 showing the needle securement area.
Figure 11:
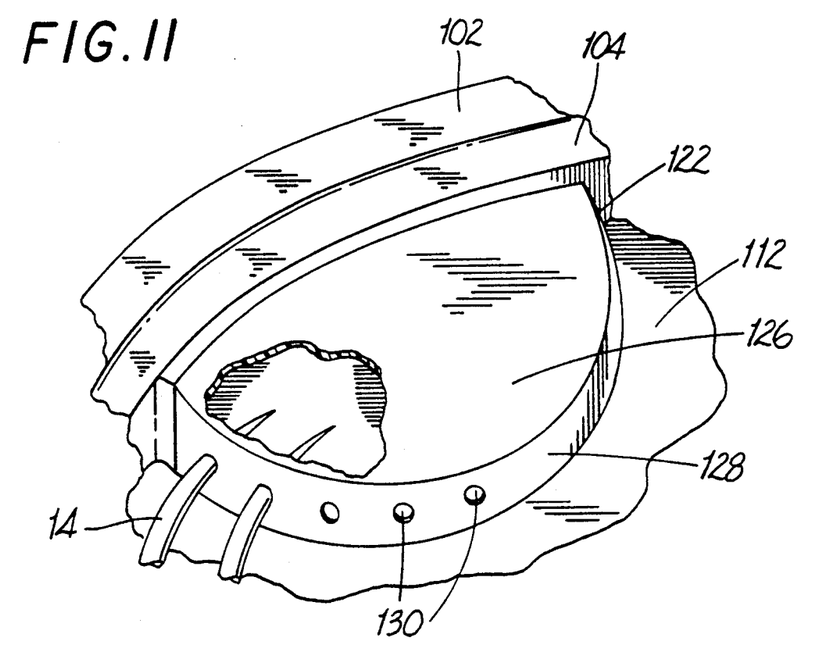
FIG. 11 is a perspective view of the needle park area of the suture retainer package of FIG. 10.
Figure 12:
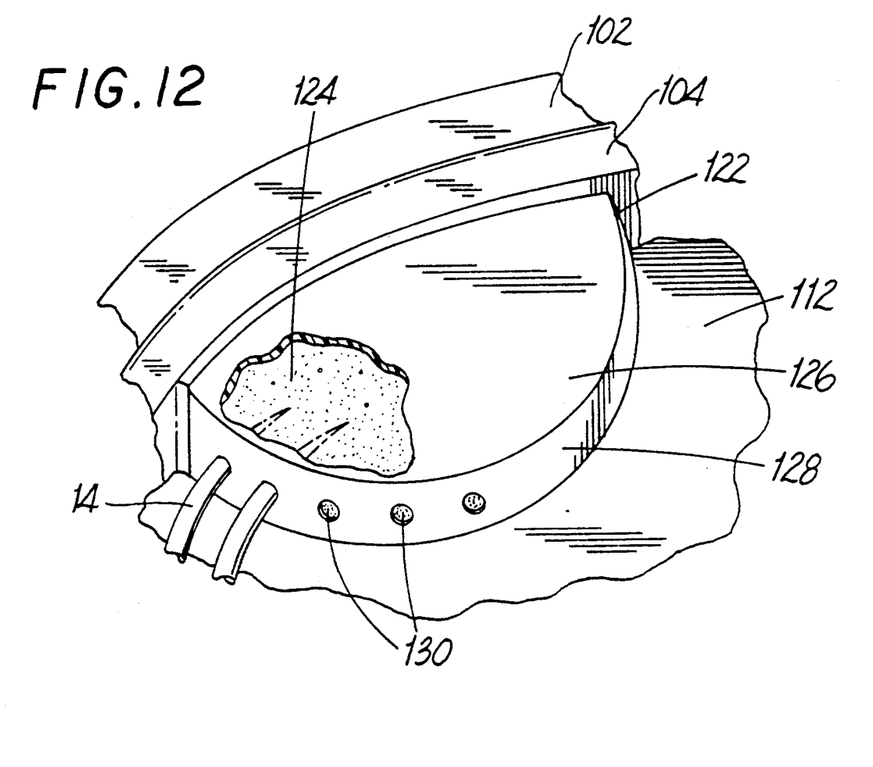
FIG. 12 is a perspective view of the needle park area of the suture retainer package of FIG. 10.

Referring to FIGS. 10-12, the needle park housing 122 has a roof section 126 and an arcuate upstanding wall section 128. A plurality of spaced apart circular portholes 130 extend through the upstanding wall section 128 terminating within the needle park housing 122. The portholes 130 themselves can be dimensioned in such a manner to securely maintain surgical needles 14 for ready removal. More particularly, as shown in FIG. 11, the diameter of the portholes 130 would be substantially equal to or less than the cross-sectional diameter of each of the surgical needles 14 so that once inserted, the surgical needle 14 would be maintained in the porthole 130 by an interference fit. Alternatively, as shown in FIG. 12, the portholes 130 can be dimensioned so as to permit surgical needles 14 to extend therethrough into the needle park housing 122, to be maintained in the sponge member 124 for ready removal.

To construct the retainer package 100 of the subject invention cover member 104 is extended into the annular recessed portion 106 of base member 102 so that the planar surface 108 of base member 102 and the planar surface 112 of cover member 104 are in face-to-face contact. At such a time sonic weldments 126 may be applied to the package at a plurality of locations spaced from the periphery of the annular cover member 104 so as to form a peripheral suture retaining channel within the annular recessed portion 106 of base member 102.

Figure 9:
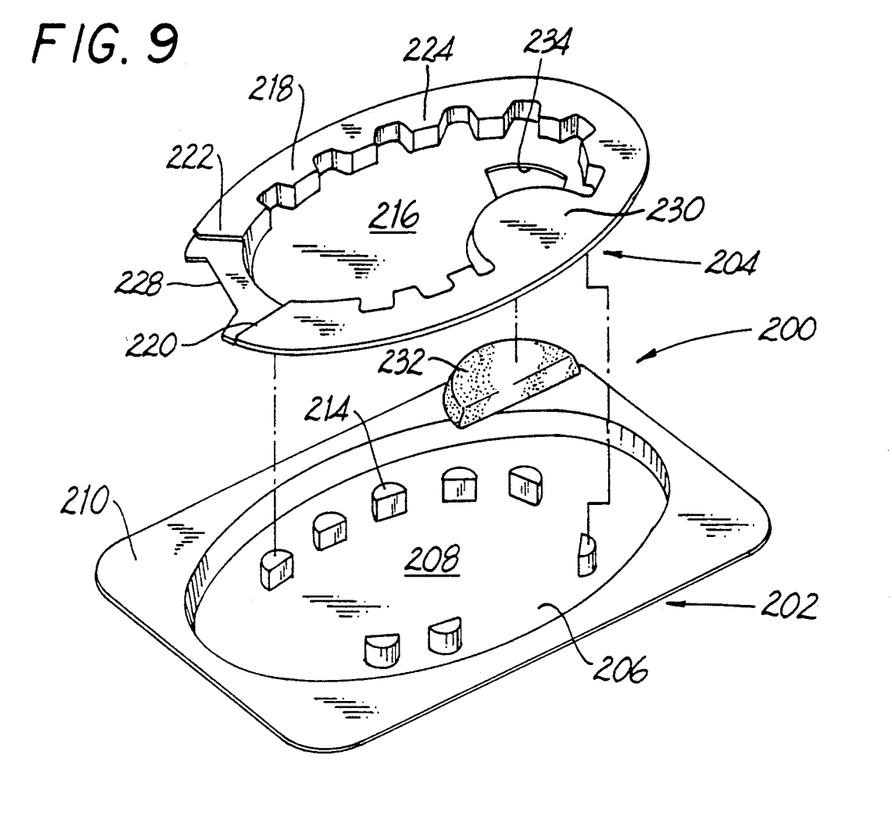
FIG. 9 is an exploded view of an alternate embodiment of the suture retainer package of the subject invention.

Turning now to FIG. 9, a third embodiment of the suture retainer package of the subject invention is illustrated and is designated generally be reference numeral 200. Retainer package 200 basically comprises a base member 202 and an annular cover member 204 of substantially elliptical configuration. Base member 202 includes an annular recessed portion 206 of elliptical configuration having a bottom surface face 208. A circumjacent flexible flange portion 210 extends outward from the periphery of the annular recessed portion 206 of base member 202. A plurality of spaced apart cones 214 extend upwardly from the bottom surface face 208 of annular recessed portion 206.

Cover member 204 includes a peripheral tunnel 218 which extends partially about the periphery of the planar surface face 216 from a first end 220 to a second end 222. Peripheral tunnel 218 is formed with a plurality of spaced apart seats 224 corresponding to said plurality of spaced apart cones 214 on base member 202. A port 228 extends inward into planar surface face 208 from the periphery thereof intermediate first and second ends 220 and 222 of the tunnel 218 for permitting passage of sutures 12 from within the retainer package 200.

A needle park housing 230 is formed in cover member 204 adjacent peripheral channel 218. A sponge member 232 is disposed in needle park housing 230 and is readily accessible for parking a plurality of suture needles 14 for ready removal. In addition, an annular slit 234 is formed in surface face 216 for permitting extension of the suture needles into the sponge member 232.

To construct the retainer package 200 of the subject invention cover member 204 is extended into the annular recessed portion 206 of base member 202 so that the planar surface 208 of base member 202 and the planar surface 216 of cover member 204 are in face-to-face contact. Furthermore, upon extending cover member 204 into annular recessed portion 206, the plurality of spaced apart cones 214 provided in annular recessed portion 206 are received in the plurality of corresponding seats 224 formed in the peripheral channel 218. At such a time, sonic weldments may be applied to the package at a plurality of locations spaced from the periphery of the annular cover member 204 so as to form a peripheral suture retaining channel within the annular recessed portion 206 of base member 202.

Although the suture retainer package of the subject invention has been described with respect to a preferred embodiment, it is apparent that changes can be made without departing from the spirit and scope of the subject invention as defined by the appended claims.

What is claimed is:

1. A package for retaining at least one armed surgical suture comprising:
   housing means having suture retention means provided therein; and
   a needle securement area integrally formed with said housing means and defining at least in part an upstanding wall section having at least one porthole extending completely therethrough dimensioned and configured to circumscribe the periphery of a surgical needle received therein.

2. A package as recited in claim 1, wherein said at least one porthole is dimensioned and positioned for maintaining a surgical needle for ready removal.

3. A package as recited in claim 1, wherein a sponge member is disposed within said needle securement area for releasably maintaining a surgical needle extending through said at least one porthole.

4. A package as recited in claim 2, wherein said housing means comprises a base having an annular recessed portion formed therein and an annular cover member mounted adjacent said annular recessed portion to form a peripheral retention channel in said recessed portion for accommodating said at least one resilient surgical suture.

5. A package as recited in claim 4, wherein said needle securement area is monolithically formed in said annular cover member.

6. A package as recited in claim 1, wherein said needle securement area comprises an arcuate upstanding wall section and a roof section.

7. A package as recited in claim 6, wherein a plurality of spaced apart portholes are defined in said upstanding wall section for accommodating a plurality of surgical needles.

8. A package as recited in claim 1, wherein said at least one porthole is substantially circular in configuration.

9. A package for retaining at least one resilient armed surgical suture comprising:
   a base member having an annular recessed portion formed therein;

an annular cover member mounted adjacent said recessed portion to form a peripheral retention channel in said recessed portion for accommodating said at least one resilient surgical suture; and a needle securement area integrally formed with said cover member and defining at least in part an upstanding wall section having at least one porthole extending completely therethrough dimensioned and configured to circumscribe the periphery of a surgical needle received therein.

10. A package as recited in claim 9, wherein said needle securement area is monolitically formed in said annular cover member.

11. A package as recited in claim 9, wherein said at least one porthole is dimensioned and positioned for maintaining a surgical needle for ready removal.

12. A package as recited in claim 9, wherein a sponge member is disposed within said needle securement area for releasably maintaining a surgical needle extending through said at least one porthole.

13. A package for retaining at least one resilient armed surgical suture comprising:

a base member having an annular recessed portion formed therein and a circumjacent flexible flange portion extending outward from said annular recessed portion;

an annular cover member mounted adjacent said annular recessed portion to form a peripheral retention channel in said recessed portion for accommodating said at least one resilient surgical suture; and a needle securement area monolithically formed with said annular cover member defining an upstanding wall section having a plurality of spaced apart circular portholes extending completely therethrough being dimensioned and configured for accommodating a plurality of surgical needles for ready removal.

14. A package as recited in claim 13, wherein a sponge member is disposed within said needle securement area for releasable maintaining surgical needles extended through said plurality of portholes.

* * * * *

UNITED STATES PATENT AND TRADEMARK OFFICE
CERTIFICATE OF CORRECTION

PATENT NO. : 5,249,673
DATED : October 5, 1993
INVENTOR(S) : Hans-Jurgen F. Sinn It is certified that error appears in the above-indentified patent and that said Letters Patent is hereby corrected as shown below:

TITLE PAGE, ITEM [73],

Assignee, "corporation" should be --Corporation--.

Column 1, line 65, after "recessed" insert --portion--.

Column 4, line 7, after "64" insert --to--.

Column 4, line 27, "16" should be --18--.

Column 4, line 28, "18" should be --16--

Column 4, line 62, "be" should be --by--.

Column 5, line 45, "be" should be --by--.

Column 6, line 45, "2" should be --1--.

Column 7, line 14, "monolitically" should be --monolithically--.

UNITED STATES PATENT AND TRADEMARK OFFICE
CERTIFICATE OF CORRECTION

PATENT NO. : 5,249,673

DATED : October 5, 1993

INVENTOR(S) : Hans-Jurgen F. Sinn

It is certified that error appears in the above-indentified patent and that said Letters Patent is hereby corrected as shown below:

Column 8, line 21, "releasable" should be --releasably--.

Signed and Sealed this

Twenty-first Day of June, 1994

Attest:

BRUCE LEHMAN

*Attesting Officer*  *Commissioner of Patents and Trademarks*